Figure 1:
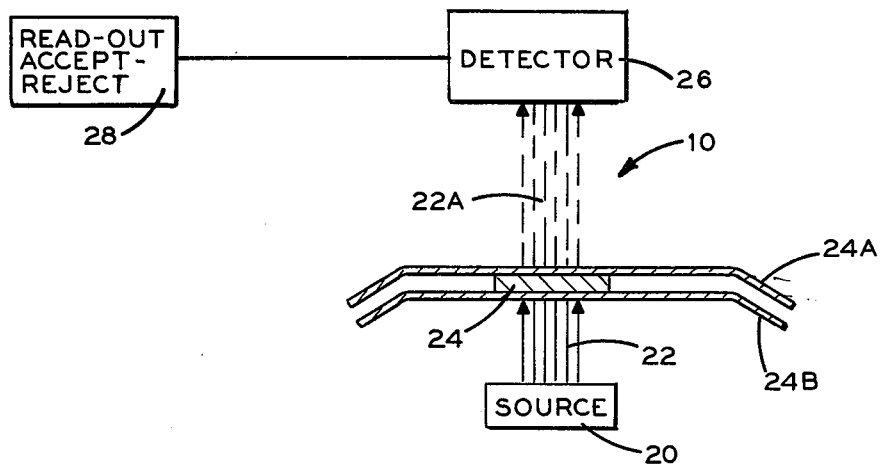

United States Patent [19]

Simmons

[11] 3,940,624
[45] Feb. 24, 1976

[54] APPARATUS AND A METHOD FOR TESTING THE INTEGRITY OF A WELD

[75] Inventor: Eugene C. Simmons, Woodbury, Conn.

[73] Assignee: P. R. Mallory & Co., Inc., Indianapolis, Ind.

[22] Filed: Nov. 29, 1972

[21] Appl. No.: 310,485

[52] U.S. Cl. .................................. 250/358 R
[51] Int. Cl. .................................. G01t 1/16
[58] Field of Search.......... 250/83.3 H, 83.3 D, 331, 250/358, 359, 360

[56] References Cited
UNITED STATES PATENTS

| | | | |
|---|---|---|---|
| 3,114,836 | 12/1963 | Fergason et al. .................. | 250/331 |
| 3,191,441 | 6/1965 | Erickson ..................... | 250/83.3 H X |
| 3,405,270 | 10/1968 | Briggs ............................ | 250/83.3 H |
| 3,462,602 | 8/1969 | Apple ............................ | 250/83.3 H |
| 3,633,031 | 1/1972 | Pesce ............................ | 250/83.3 D |

Primary Examiner—James W. Lawrence
Assistant Examiner—Davis L. Willis
Attorney, Agent, or Firm—Israel Nissenbaum; Ronald Cornell; Charles Hoffmann

[57] ABSTRACT

A beam of spectral energy is directed onto a weld spot and the integrity of the weld is measured by the strength of the reflected beam or of the transmitted beam, which may also involve a function of the refractive characteristic effect of the weld spot on the incident beam.

6 Claims, 2 Drawing Figures

APPARATUS AND A METHOD FOR TESTING THE INTEGRITY OF A WELD

This invention relates to a method for testing the structural integrity of spot welds between two metals by a non-destructive test.

The field of application of the invention is in the manufacture of electrical energy cells. The components of the electric cell are inserted into a can which is then sealed with a cover top embodying a metal cover and an insulating grommet that is appropriately pressed between the cover and the upper end of the can to establish a hermetic seal. The sealing action is usually achieved by peening over the open rim edge of the can onto the grommet and thereby impressing a compression force on the grommet with respect to a backup element in the can, which may be an elemental portion of the can, physically displaced to serve as a seating annulus, and a compression reaction element for the sealing grommet.

In certain of such cells, the top closure cover is formed of two metal discs, originally separate, in order to permit simpler assembly of the one inner cover disc to a component with the cell, with the outer cover disc finally welded to such inner disc, so the outer disc may serve as an accessible terminal element of the cell for connection to an external circuit.

In order to provide good electrical conductivity between the two top closure discs, they are spot welded at one or more areas.

If those spot welds are not properly effected, the transmitting conductivity of the electric welds are not adequate, and are defective, and are not satisfactory as current conducting elements for the cell, and as a result, an electric cell that is completely assembled with such a defective cell top would itself be defective and inoperative and rejectable.

At present, in conventional procedures, sample tests are made of production runs of such spot welding, with periodic samples selected at ramdom. Usually, such parts are subjected to a visual inspection for surface defects, and then the welded parts are physically separated to test the strength of the weld and to check the extent or diameter of the weld spot as determineed by size of the "nugget". The entire lot is then accepted or rejected on the basis of these individually tested and randomly selected parts. The limitations of the present conventional method are several:

1. Assembled parts are destroyed for testing
2. High probability of rejecting acceptable parts.
3. High probability of accepting rejectable parts.
4. Time consuming.
5. Dependence upon the technique of the inspector, and his ability to judge his results.
6. The inability of sorting lots on a continuous basis.

A primary object of this invention is to provide a non-destructive test method for determining the integrity and reliability of the weld.

Another object of this invention is to provide a method for testing the integrity and reliability of a weld, by subjecting the welded region to a beam of spectral energy and measuring the ratio of the transmitted energy relative to the strength of the incident beam.

Another object of this invention is to provide a method for testing the integrity and reliability of a weld by subjecting the welded region to a beam of spectral energy and measuring the refractive index, or change in refractive index, as an indicator of the integrity of the weld.

Another object of the invention is to provide a test method for testing the integrity of the weld, that can be performed as a production line operation, immediately after the weld, and with a minimum of checking and testing time.

Another object of the invention is to provide a method of controlling the welding machine to correct a welding operation that is not proper, by utilizing the read-out from the testing method of this invention.

Another object of this invention is to provide a weld testing method in which the tests on the weld can be performed as the welded parts are transferred along the production line, or if accummulated, can be tested individually as a quick and simple operation within a few seconds.

Another object of the invention is to provide a weld testing method in which the welded region is subjected to a beam of spectral energy, and the integrity of the weld is measured as a function of the energy-transmitting ability of the weld.

In accordance with the present invention, a test specimen is subjected to a beam of spectral energy, and the amount of energy transmitted, or absorbed, is measured to provide an accurate profile of the density and configuration of the weld.

The beam of spectral energy may be supplied from various sources. In one set of tests, a calibration source of Co60 was used, to apply the beam energy, with a gas filled detector to measure the transmitted energy, dependent upon the avalanche effect for readings. The gamma radiation absorbed by the weld was related to the density, and test samples showed that 90% accuracy could be obtained by this method. Based on the above described data it was calculated that sources such as Strontium 90 (a beta emitter), seen as Yttrium 90, could be used in a three to ten micro curie range. An end readout Beta/Gamma counter tube filled with a Ne, A, or halogen as a detector, and a readout such as a Baird 530, would provide 100% accuracy within the limits that are required.

The above materials were considered among those within the very short wave length range and high energy levels.

In the mid range energy levels from about 4,000 to 7,000 angstroms, the amount of heat transmitted by a beam pulse of energy as, for example, from an I.R. emitting diode of the qallium arsenide type, provides a measure of the weld strength. One form of heat detector, for example, utilized liquid crystals on a mylar sheet on the weld region, as an indicator with a suitable optical readout.

In experimental tests made at low range energy level, at about 10,000 angstroms, significally accurate readings were obtained in the visible light spectrum with the use of heat. The tests within the range of 10,000 to 14,000 angstroms with a 30° to 40°C change in temperature above ambient seem to provide the most favorable working conditions with greatest accuracy.

Figure 2:
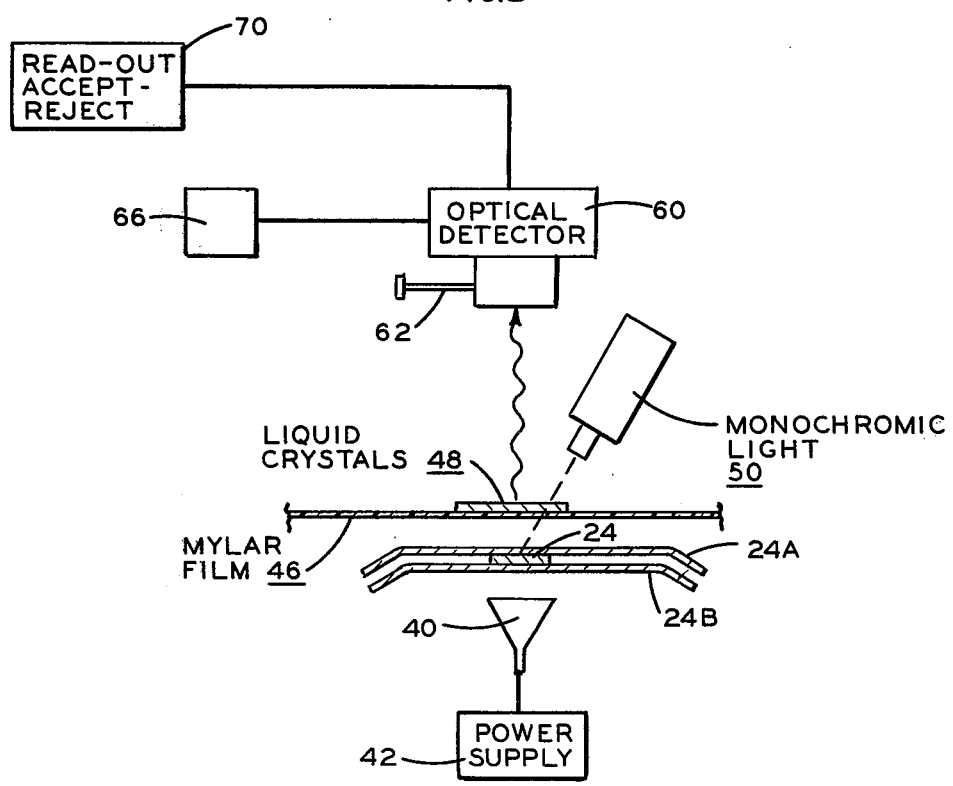

The general arrangement of the test system is described in more detail in the following specification taken together with the annexed drawings, in which FIG. 1 is a schematic layout of the basic system of this invention; and FIG. 2 is a modified form of system utilizing a heat responsive system of liquid crystals on a Mylar film, irradiated with monochromatic light with an infrared beam generating source.

The invention generally relates to a system for measuring the integrity of a weld, particularly a spot weld, by directing an incident beam of spectral energy onto the welded spot region, and measuring the ratio of the energy content of the transmitted beam directly, or as refracted, to the energy content of the incident or applied beam. The measurement would be of the absorption and thus of the weld density.

As shown in FIG. 1, a system 10 embodying the principles of this invention, is indicated as including a source 20 of spectral energy for generating and directing a beam 22 through a welded spot 24 that is to be tested for the integrity of the spot weld between two cover elements 24A and 24B, for an electric cell closure, with the transmitted beam 22A collected by a properly positioned detector 26 whose detection value will be indicated in a readout indicator 28.

The source of spectral energy may be a samplee of cobalt-60 or strontium-90. These elements are indicated merely as typical or suitable. The source may be any gamma emitter or beta emitter, or equivalent.

It is clear that the measurement of the energy received by the detector 26 will be a function of the transmitted beam 22A, and that quantity will be related to the weld as a differential function between the energy of the applied incident beam 22 less the energy of the transmitted beam 22A.

In the installation of such a system for the industrial application in testing the integrity of the spot weld, the strength of the incident energy beam 22 can be initially computed and established, and the detector 26 then adjusted to read the transmitted energy from the transmitted beam as being low enough to indicate a spot weld whose integrity will be adequate to serve as a good electric conductive weld, in which case the detector will energize its readout indicator 28 to show a satisfactory indication such as GREEN or YES or GO. If the energy in the transmitted beam is too strong, it will energize the detector beyond a predetermined adjusted value set to indicate a satisfactory weld, and thus the amount of energy absorbed by the detector will be sufficient to cause a reading beyond that adjusted adequate value, and the indication of the readout device 28 will then indicate any suitable indication to indicate and represent REJECT.

The operation of the detector 26 may be controlled to read a ratio or part of the incident beam, by adjusting the detector to the strength of the incident beam as unity; or the detector may be controlled to read a difference value between the incident beam energy and the transmitted beam energy. Suitable measurements of the incident beam strength may be used to control the detector 26 according to the type of read out measurements desired.

FIG. 2 shows an optical system for measuring the integrity of the weld by measuring the refractive index, or the change in the refractive index, of a material responding to temprature developed in the weld spot by an applied heat beam incident to one side of the weld, and the developed temperature measured on the other side of the weld, as a function of the quality of the weld.

As shown in FIG. 2, a source 40 of infra-red rays is controlled from an electronic power supply 42 to establish a relatively constant temperature condition in the source 40, for radiating and directing an infra-red beam onto one side of the weld spot to be tested. The quality of the weld will determine the amount of energy absorbed or reflected by the weld spot, and thus, in turn, will determine the temperature that will be deveoped in and transmitted by the weld spot, which can then be measured on the other side of the weld spot as output temperature.

In order to obtain a measure of the output temperature of the weld spot, a small volume of liquid crystals 48 are placed on a mylar film 46, that is in contact with the weld spot, so the liquid crystals will be affected by the output temperature of the weld spot without actually touching the welded metal.

A source 50 of monochromatic light is positioned to direct an incident beam on the crystals heated by the weld spot, and the variable refractive character of the crystals will modify the incident light beam to produce a reflected refracted beam 64, with a degree of refraction related to the temperature of the liquid crystals, which temperature will, in turn, be a function of the output temperature of the weld spot. Thus, the reflected refracted beam 64 is measured by an optical detector 60 with an adjustable control slot 62 for selectively accepting a predetermined width of the reflected refracted beam 64. The adjustment of the detecting slot 62 is predetermined and precalibrated with respect to a present constant value of the incident beam adjusted to a satisfactory unit value. The optical detector 60 may be of electronic type, in which case appropriate electronic control equipment 66 serves to maintain the optical detector in suitable operating condition.

The output of the optical detector 60 is then supplied to a suitable readout device 70 which will indicate, from the value of the signal to the readout, whether the spot weld is acceptable or is to be rejected.

By maintaining the infra-red source 40 at a constant value, and the monochromatic light and the optical detector appropriately calibrated to each other, the output reading from the optical detector will provide an immediate reading of the quality of the weld spot as being acceptable or nonacceptable, all without affecting or destroying the welded unit under test.

The control slot 62 for the optical detector provides a means for accepting all or a selected portion of the output beam transmitted from the weld spot.

Thus, by the systems and methods shown herein, the integrity of a weld can be checked and measured by measuring the transfer characteristics of the weld spot in directly modulating a transmitted beam of spectral energy; or in thermally modulating an optical system in which a temperaturesensitive crystal, that varies its refractive index with temperature, serves to measure and indicate the heat transfer characteristic of the weld spot bond; both methods serving thereby to indicate the condition of the weld bond as to acceptability or non-acceptability equivalent to rejectable.

The systems shown may be modified by the use of various equivalents, without departing from the spirit and scope of the invention, as defined in the claims.

What is claimed is:

1. The method of testing the structural integrity of a composite weld between two metal plates used as a terminal element and closure for a battery which comprises the steps of:
   1. placing a material adjacent to and in contact with a first side of the weld spot area of the test specimen, the refractive index of said material measurably varying in response to varying temperatures transmitted thereto from the test specimen, the temperature transmitted being a function of the density of the weld between the two metal plates;

2. directing an incident beam of monochromatic light on a first side of said material of step (1), said beam of light emitted from a source positioned adjacent said material of step (1);

3. heating the test specimen by subjecting the second side thereof to a beam of infrared energy;

4. determining the integrity of the weld by measuring the degree of refraction of the reflected, refracted beam of monochromatic light by means of a detector device, the degree of refraction of said incident light beam being a function of the temperature of the material of step (1), which in turn is a function of the output temperature of the spot weld.

2. The method of claim 1 wherein said material adjacent to the weld spot area comprises a volume of liquid crystals.

3. The method of claim 2 wherein an indicator is energized by said detector.

4. Apparatus for testing a spot weld between two metal discs used as a terminal element and closure for a battery comprising:

1. means for heating the specimen to be tested for the integrity of the weld, said means comprising a source of infrared energy disposed on a first side of said test specimen;

2. a material placed adjacent to and in contact with the second side of the weld spot area of the test specimen, said material characterized by a refractive index which measurably varies in response to varying temperatures transmitted thereto;

3. a source of monochromatic light disposed adjacent said material whose index of refraction is being varied such that an incident beam of light may be directed on said material;

4. a detector for measuring the degree of refraction of the incident beam of monochromatic light directed on said material disposed adjacent to the weld spot area of the test specimen;

5. and an indicator to be energized from said detector.

5. Apparatus as in claim 4, in which said material adjacent to the weld spot area comprises a volume of liquid crystals.

6. Apparatus as in claim 5, in which said source of infrared energy is a diode of the gallium arsenide type.

* * * * *